US00PP33717P3

(12) United States Plant Patent
Bell

(10) Patent No.: US PP33,717 P3
(45) Date of Patent: Dec. 7, 2021

(54) BLUEBERRY PLANT NAMED 'RIDLEY1702'

(50) Latin Name: ***Vaccinium* hybrid**
Varietal Denomination: Ridley1702

(71) Applicant: MOUNTAIN BLUE ORCHARDS, PTY LTD, Lindendale (AU)

(72) Inventor: Ridley Bell, Lindendale (AU)

(73) Assignee: Mountain Blue Orchards, Pty Ltd, Lindendale (AU)

( * ) Notice: Subject to any disclaimer, the term of this patent is extended or adjusted under 35 U.S.C. 154(b) by 0 days.

(21) Appl. No.: 17/178,640

(22) Filed: Feb. 18, 2021

(65) Prior Publication Data

US 2021/0274693 P1 Sep. 2, 2021

Related U.S. Application Data

(60) Provisional application No. 62/979,329, filed on Feb. 20, 2020.

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC ... A01H 5/08; A01H 5/02; A01H 5/00; A01H 6/36; A01H 6/368
See application file for complete search history.

(56) References Cited

U.S. PATENT DOCUMENTS

PP25,432 P3 4/2015 Bell

*Primary Examiner* — June Hwu
(74) *Attorney, Agent, or Firm* — Plant & Planet Law Firm

(57) ABSTRACT

The new blueberry plant variety 'Ridley1702' is provided. 'Ridley1702' is a commercial variety intended for use as fresh fruit for shipping, hand pick, customer pick, machine harvest and processing markets and as a home garden plant. The variety is produced from a cross of 'Ridley1403' and 'Ridley1812', which can be distinguished by its outstanding features.

7 Drawing Sheets

Latin name of the genus, and species:
Genus—*Vaccinium.*
Species—hybrid.
Variety denomination: The new blueberry plant claimed is of the variety denominated 'Ridley1702'.

BACKGROUND OF THE INVENTION

The present invention relates to a new and distinct perennial variety of *Vaccinium* hybrid (Southern Highbush Blueberry), which has been given the variety denomination of 'Ridley1702'. Its market class is that of a fruiting plant. 'Ridley1702' is intended for use as fresh fruit for shipping, customer pick and processing markets and as a home garden plant.

The new *Vaccinium* hybrid variety is a selection resulting from seedlings produced in a breeding program of *Vaccinium* at Lindendale, NSW, Australia in 2011 from the controlled pollination of seed parent 'Ridley1403' (U.S. Plant Pat. No. 25,432) with pollen parent 'Ridley1812' (not patented). The new variety was discovered and selected as a single plant within a population of 100 resulting *Vaccinium* hybrid plants from this controlled pollination in 2014 in a commercial field plantation environment at Tabulam, New South Wales, Australia. Selection criteria were a combination of strong plant growth vigor, upright/whippy plant growth habit, mid-season time of flowering and fruit ripening, ease of harvest, very large fruit, good flavor, very firm, very crunchy, loose clusters and very good bloom.

The selection was subsequently evaluated for a number of years at the commercial farms at Tabulam, New South Wales, Australia.

Asexual reproduction of the new variety by cutting propagation since 2014 at Lindendale, New South Wales, Australia has demonstrated that the new variety reproduces true to type with all of the characteristics, as herein described, firmly fixed and retained through successive generations of such asexual propagation.

SUMMARY OF THE INVENTION

The new *Vaccinium* hybrid variety is a selection resulting from seedlings produced in a breeding programme of *Vaccinium* at Lindendale, NSW, Australia in 2011 from the controlled pollination of seed parent 'Ridley1403' (U.S. Plant Pat. No. 25,432) with pollen parent 'Ridley1812' (not patented). The seed parent was produced from a seedling selection of 'S02-25-05' (not patented) and pollen parent 'S03-08-02' (not patented). The pollen parent was produced from a seedling selection of 'S01-28-01' (not patented) and pollen parent 'S01-23-01' (not patented).

Plants of the new variety differ from plants of the seed parent 'Ridley1403' primarily in bush structure being upright/whippy, larger fruit size, stronger bloom, firmer and crunchier berries and better suitability to machine harvest. Plants of the new variety differ from plants of the pollen parent 'Ridley1812' primarily in having an earlier season and larger fruit size with firmer and crunchier berries that are better suited to machine harvest.

The new blueberry variety was designated 'Ridley1702', and has been planted in replicated trials since 2017.

The new *Vaccinium* hybrid variety is a selection resulting from seedlings produced in a controlled breeding program of *Vaccinium* at Lindendale, NSW, Australia from the controlled pollination in 2011 of seed parent 'Ridley1403' with pollen parent 'Ridley1812'.

Asexual reproduction of the new variety by softwood cutting propagation since 2014 at Lindendale, New South Wales has demonstrated that the new variety reproduces true to type with all of the characteristics, as herein described, firmly fixed and retained through successive generations of such asexual propagation.

The new *Vaccinium* hybrid variety is a selection resulting from seedlings produced in a breeding program of *Vaccinium* at Lindendale, NSW, Australia in 2011 from the controlled pollination of seed parent 'Ridley1403' with pollen parent 'Ridley1812'. The new variety was discovered and selected as a single plant within a population of 100 resulting *Vaccinium* hybrid plants from this controlled pollination in 2014 in a commercial field plantation environment at Tabulam, New South Wales, Australia. Selection criteria were a combination of strong plant growth vigor, upright/whippy plant growth habit, mid-season time of flowering and fruit ripening, ease of harvest, very large fruit, good flavor, very firm, very crunchy, loose clusters and very good bloom.

The selection was subsequently evaluated for a number of years at the commercial farms at Tabulam, New South Wales, Australia.

The following characteristics of the new variety have been repeatedly observed and can be used to distinguish 'Ridley1702' as a new and distinct variety of *Vaccinium* hybrid plant:

1. Upright/whippy growth habit
2. Strong plant vigor
3. High yield
4. Early season
5. Very crunchy
6. Very firm
7. Good (sweet) flavor
8. Loose clusters
9. Very good bloom
10. Very large fruit size
11. Suitability to machine harvest Plants of the new variety differ from plants of the seed parent 'Ridley1403' primarily in bush structure being upright/whippy, larger fruit size, stronger bloom, firmer and crunchier berries and better suitability to machine harvest. Plants of the new variety differ from plants of the pollen parent 'Ridley1812' primarily in having an earlier season and larger fruit size with firmer and crunchier berries that are better suited to machine harvest.

Asexual reproduction of the new variety by cutting propagation since 2014 at Lindendale, New South Wales, Australia has demonstrated that the new variety reproduces true to type with all of the characteristics, as herein described, firmly fixed and retained through successive generations of such asexual propagation.

BRIEF DESCRIPTION OF THE DRAWINGS

The accompanying photographic illustration shows typical specimens in full color of the foliage and fruit of the new variety 'Ridley1702'. The colors are as nearly true as is reasonably possible in a color representation of this type.

Figure 1:
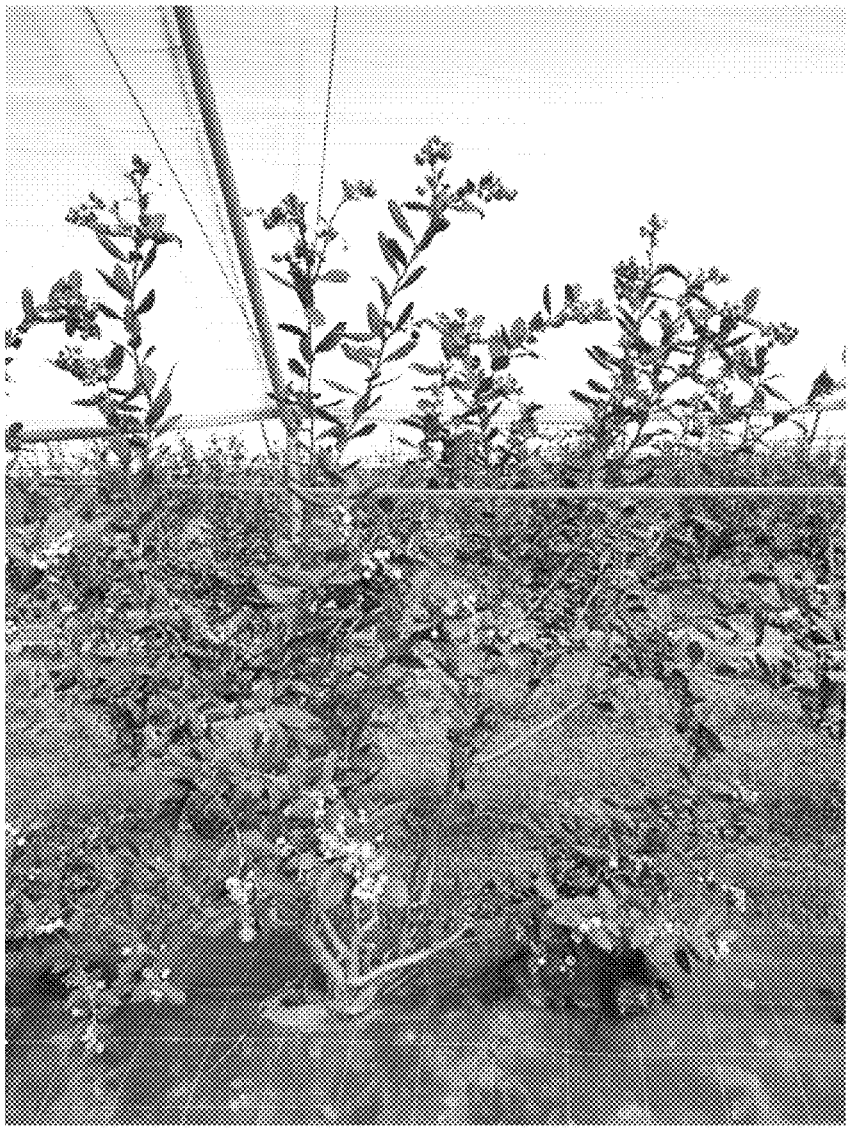
FIG. 1 is a photograph of the new variety 'Ridley1702', demonstrating the plant's upright/whippy growth habit.
Figure 2:
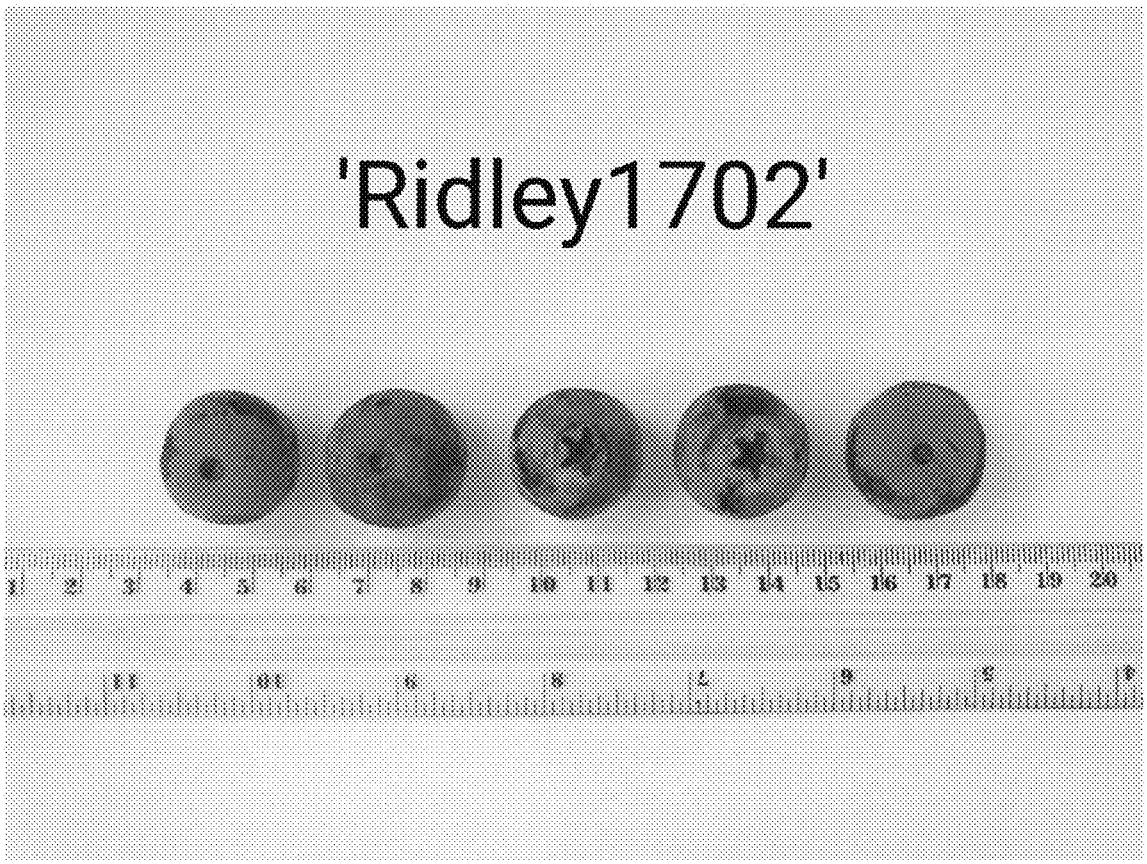
FIG. 2 is a photograph of the fruit of the new variety 'Ridley1702'.
Figure 3:
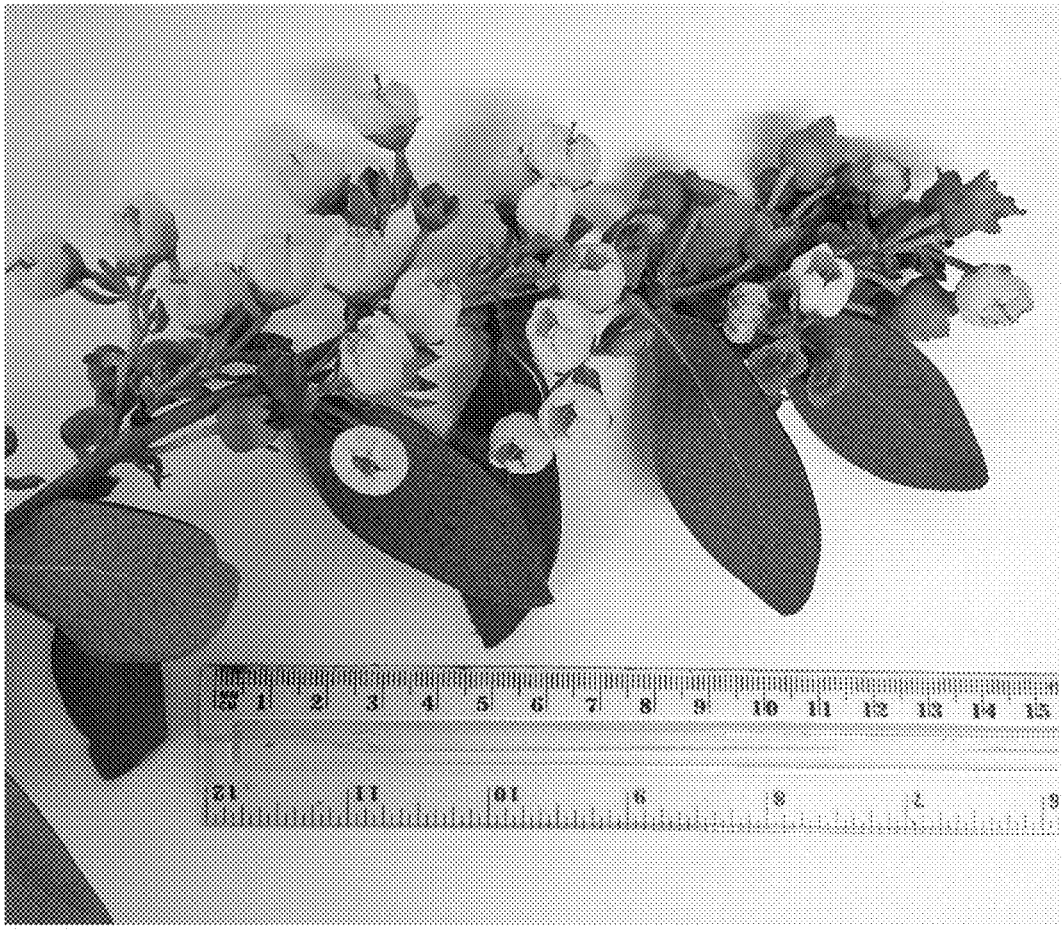
FIG. 3 is a photograph of the flowers of the new variety 'Ridley1702'.
Figure 4:
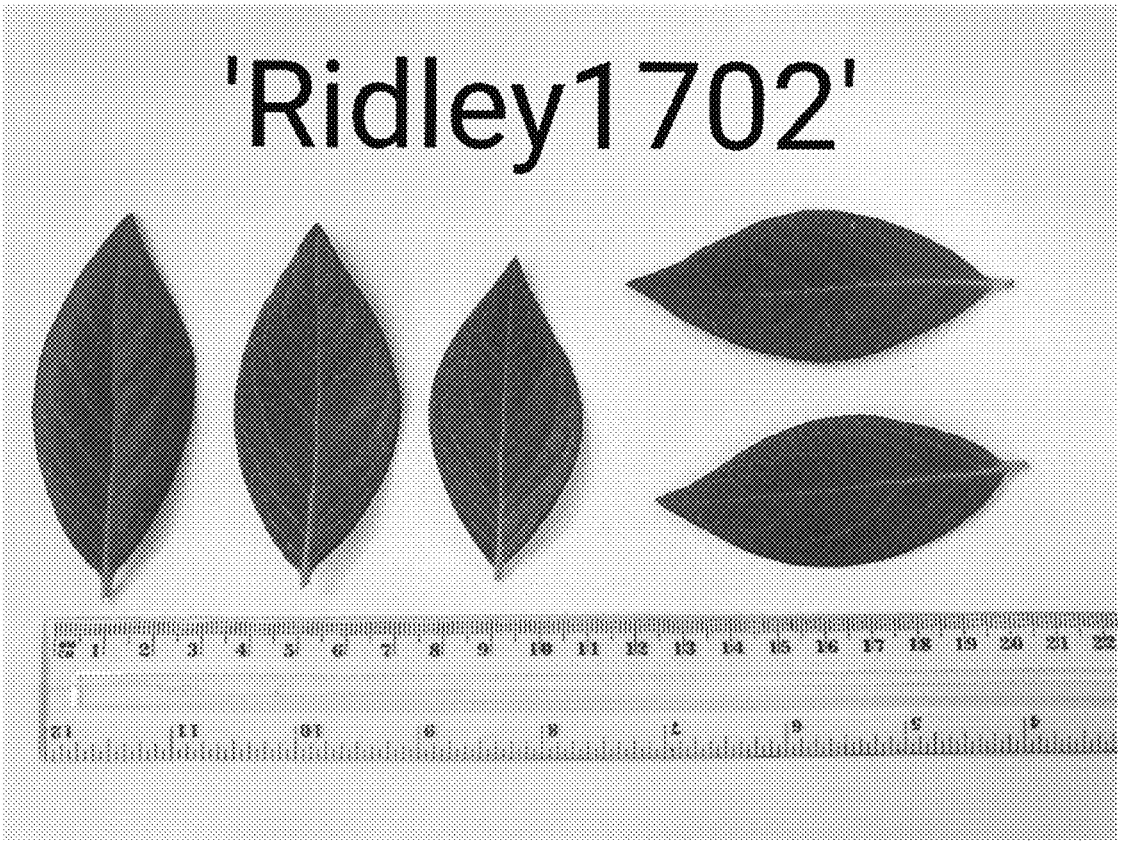
FIG. 4 is a photograph of the leaves of the new variety 'Ridley1702'.
Figure 5:
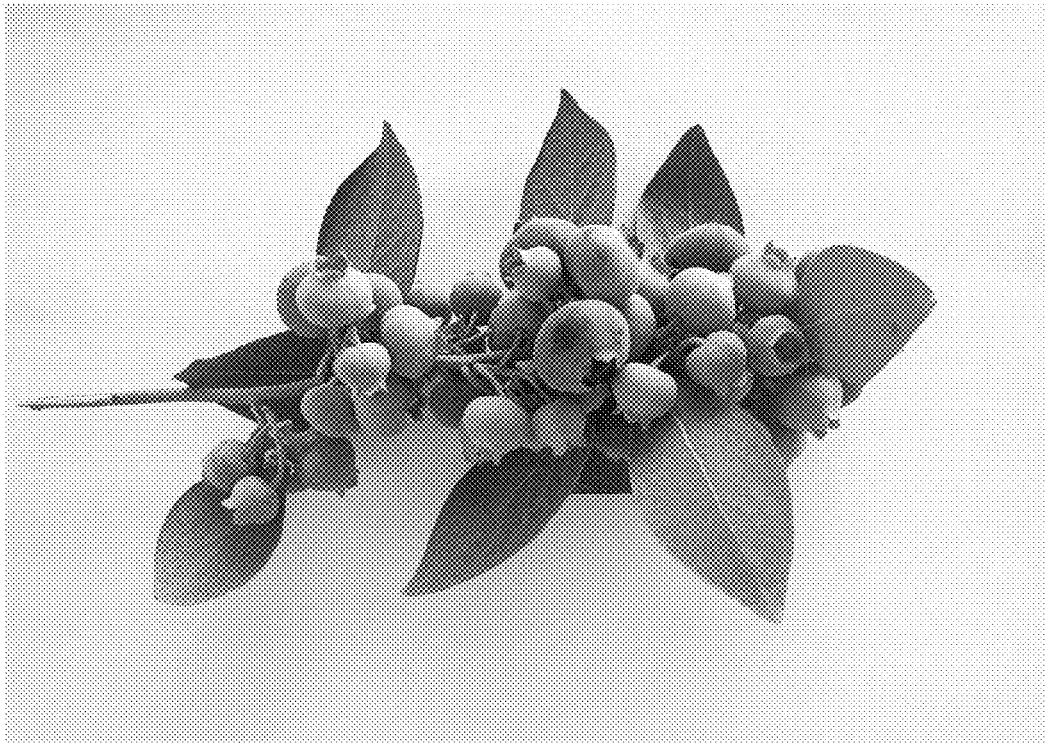
FIG. 5 is a photograph of the leaves, fruit, new shoot and fruit cluster of the new variety 'Ridley1702'.
Figure 6:
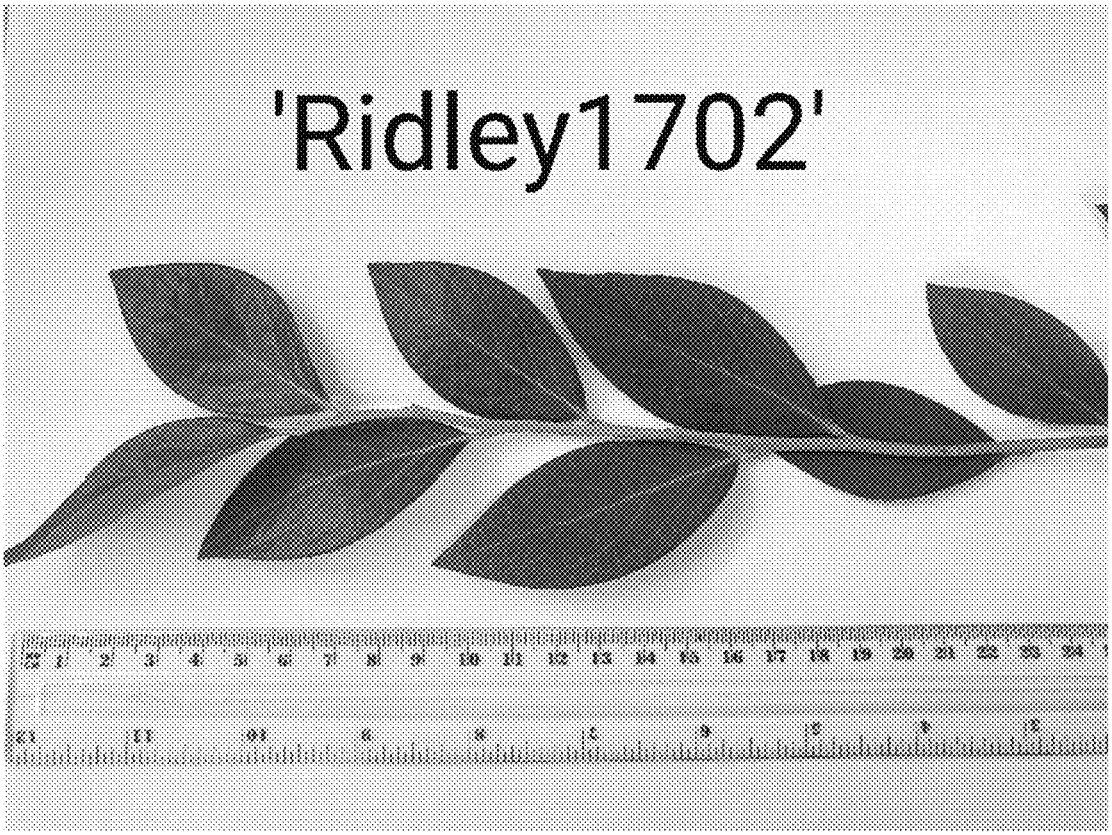
FIG. 6 is a photograph of a vegetative shoot of the variety 'Ridley1702'.
Figure 7:
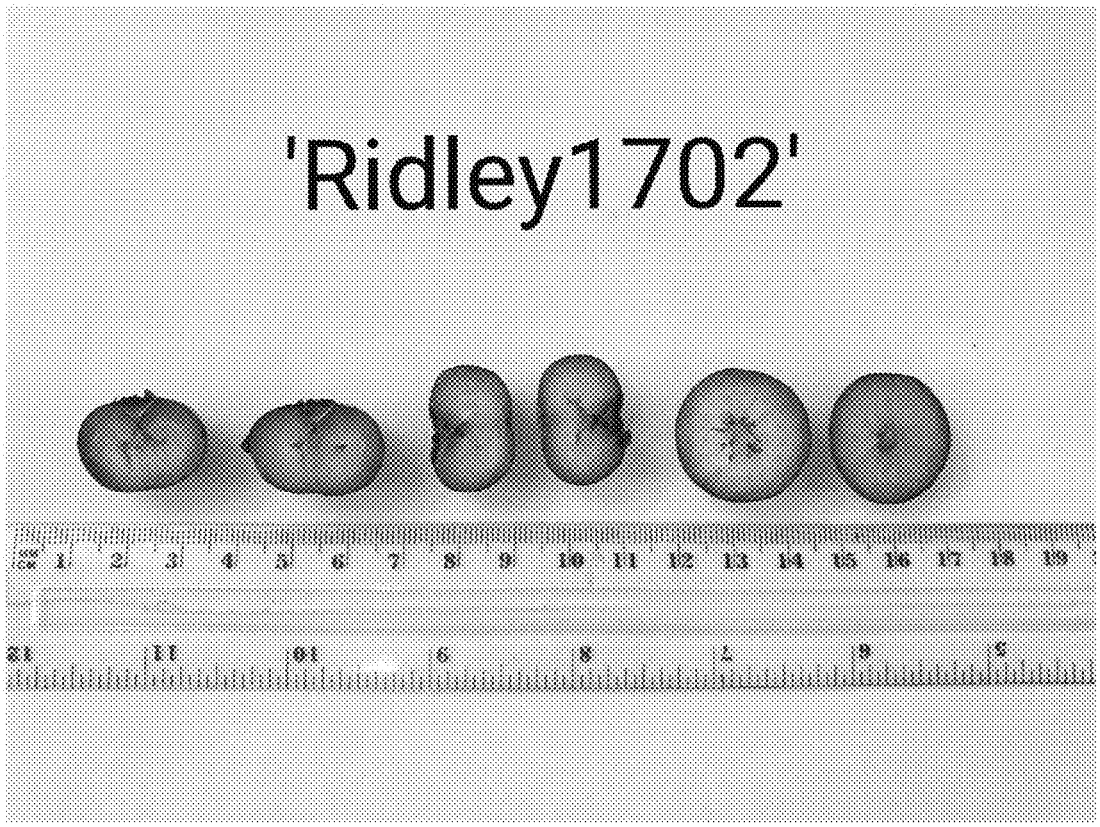
FIG. 7 is a photograph of fruit cross section of the variety 'Ridley1702'.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'Ridley1702'. The data which define these characteristics were collected from asexual reproductions of the original selection. Dimensions, sizes, colors, and other characteristics are approximations and averages set forth as accurately as possible. The plant history was taken on plants approximately 1-2 years of age, and the descriptions relate to plants grown in the field in Tabulam, New South Wales, Australia. Descriptions of fruit characteristics were made on fruit grown in Tabulam, New South Wales, Australia. Color designations are from Tabulam, New South Wales, Australia. Color notations are based on *The Royal Horticultural Society Colour Chart*, of The Royal Horticultural Society, London, sixth edition.

Classification:

a. *Family*.—Ericaceae.
b. *Genus*.—*Vaccinium*.
c. *Species*.—hybrid.
d. *Common name*.—Southern Highbush Blueberry.

Parentage: Female Parent.—'Ridley1403'. Male Parent.—'Ridley1812'.

Market class: a fruiting plant intended for use as fresh fruit for shipping, hand pick, customer pick, machine harvest and processing markets and as a home garden plant.

PLANT

General:

*Parentage*.—Female Parent — 'Ridley1403'. Male Parent — 'Ridley1812'.
*Plant height*.—1.4-1.8 m (1.68 m).
*Plant width*.—1-1.5 m (1.25 m).
*Growth habit*.—Upright/whippy.
*Growth*.—Strong.
*Productivity*.—5.3 kg/plant on 2-year old bushes.
*Leafing*.—Vegetative bud burst is medium.
*Twigginess*.—Low to moderate.

STEM

General:

*Suckering tendency*.—Low; <5 canes/plant.
*Mature cane color*.—199D/197D.
*Mature cane length*.—1.2-1.6 m.
*Mature cane width*.—1.5-2.8 cm.

*Bark texture*.—Medium roughness (typical of species).
*Surface texture of new wood*.—Smooth.
*Internode length on strong, new shoots*.—18-22 mm.
*Fruiting wood*.—To 15-16 cm in length.

FOLIAGE

General:
*Time of beginning of leaf bud burst*.—Medium.
*Leaf color* (*top side*).—146A/141A.
*Leaf color* (*under side*).—138B/C.
*Leaf arrangement*.—Alternate.
*Leaf shape*.—Elliptic.
*Leaf margins*.—Entire.
*Undulation of margin*.—Weak.
*Leaf venation*.—Reticulate.
*Leaf apices*.—Acute.
*Leaf bases*.—Obtuse.
*Leaf length*.—65-80 mm (73.1).
*Leaf width*.—33-38 mm (35.3).
*Leaf length/width ratio*.—1:1.97 to 1:2.11.
*Leaf nectaries*.—Absent.
*Pubescence of upper side*.—Absent.
*Pubescence of lower side*.—Absent.
*Cross sectional profile*.—Flat.
*Longitudinal profile*.—Straight.
*Attitude*.—Semi-upright.
Petioles:
*Length*.—3.5-6 mm (4.9).
*Width*.—2-2.5 mm (2.2).
*Color*.—144D/142C.

FLOWERS

General:
*Time of beginning of flowering*.—~Week 17-20 at Tabulam, NSW Australia.
*Time of* 50% *anthesis*.—~Week 27-31 at Tabulam, NSW Australia.
*Flower shape*.—Urceolate.
*Flower bud density*.—7-10 buds/lateral.
*Flower fragrance*.—Weak (sweet smelling).
Corolla:
*Color*.—White 155A/C.
*Length*.—8-10 mm.
*Width*.—9-11 mm.
*Aperture width*.—4-6 mm.
*Anthocyanin coloration of corolla*.—Nil.
*Corolla ridges*.—Present.
*Protrusion of stigma*.—Yes (1-2 mm).
Inflorescence:
*Length*.—40 to 80 mm.
*Diameter*.—30-45 mm.
*Length of peduncle*.—~30-35 mm.
*Surface texture of peduncle*.—Smooth.
*Color of peduncle*.—144C/145A.
*Length of pedicel*.—~10-18 mm.
*Surface texture of pedicel*.—Smooth.
*Color of pedicel*.—144C/145A.
*Number of flowers per cluster*.—6-10 flowers/bud.
*Flower cluster density*.—Loose to Medium.
Calyx (with sepals):
*Diameter*.—6-8 mm (6.9).
*Color* (*sepals*).—203B/C.
Stamen:
*Length*.—7-9 mm.
*Number per flower*.—Approximately 10-12.
*Filament color*.—142C.
Pistil:
*Length*.—10-13 mm.
*Style Length*.—7-10 mm.
*Ovary color* (*exterior*).—146A/146B/144A.
Anther:
*Length*.—4-5 mm.
*Number*.—Approximately 10-12.
*Color*.—163A/N167A.
Pollen:
*Abundance*.—Medium-high
*Self-compatibility*.—99% in self-pollination tests.

FRUIT

General:
*Time of fruit ripening*.—Week 24-29 (at Tabulam NSW, Australia)
*Time of* 50% *maturity*.—Week 36-41 (at Tabulam, NSW, Australia).
*Fruit development period*.—55-65 days (at Tabulam, NSW, Australia).
*Cluster density*.—Loose at about 35-45 berries per branch.
*Unripe fruit color*.—144A/143A.
*Ripe berry color*.—Without bloom 203B/C.
*Berry surface wax abundance*.—Strong.
*Berry flesh color*.—155C.
*Berry weight*.—Avg. 3.75 g.
*Berry height from calyx to scar*.—~15 mm.
*Berry diameter*.—Avg. 20.9 mm.
*Berry shape*.—Oblate.
*Fruit stem scar*.—Small (dry).
*Sweetness when ripe*.—Medium-high.
*Firmness when ripe*.—Very firm.
*Acidity when ripe*.—Low/medium.
*Storage quality*.—Good, lasted 6-8 weeks at 0-2 degrees Celsius in tests. Not tested with modified atmosphere storage yet.
*Suitability for mechanical harvesting*.—Very firm fruit firmness and ease of picking/shakeability suited to machine harvest.
*Self-fruitfulness*.—99% fruit set with own pollen in tests at Lindendale, NSW Australia.
*Uses*.—Fresh fruit for shipping, customer pick and processing markets and as a home garden plant.

COMPARISON BETWEEN PARENTAL AND COMMERCIAL VARIETIES

TABLE 1

| Organ | Context | 'Ridley1702' |
|---|---|---|
| Plant | vigor | strong |
| Plant | growth habit | Upright/whippy |
| One-year-old shoot | color | green |
| One-year-old shoot | length of internode | medium |
| Leaf | length | long |
| Leaf | width | broad |
| Leaf | shape | elliptic |
| Leaf | color of upper side | green |
| Leaf | intensity of green color on upper side (varieties with green leaf color only) | medium |

TABLE 1-continued

| | | |
|---|---|---|
| Leaf | margin | entire |
| Flower bud | anthocyanin coloration | weak |
| Flower | shape of corolla | urceolate |
| Flower | size of corolla tube | medium |
| Flower | anthocyanin coloration of corolla tube | absent or very weak |
| Flower | ridges on corolla tube | present |
| Fruit cluster | density | Medium-loose |
| Unripe fruit | intensity of green color | light |
| Fruit | size | Very large |
| Fruit | shape in longitudinal section | oblate |
| Fruit | attitude of sepals | erect |
| Fruit | diameter of calyx basin | large |
| Fruit | depth of calyx basin | deep |
| Fruit | intensity of bloom | Medium to strong |
| Fruit | color of skin | Dark blue |
| Fruit | firmness | very firm |
| Fruit | sweetness | Medium to high |
| Fruit | acidity | Low to medium |
| Time of | vegetative bud burst | medium |
| Time of | beginning of flowering | medium |
| Time of | beginning of fruit ripening | medium |

| Organ | 'Ridley1812' | 'Ridley1403' (U.S. Plant Pat. No. 25,432) |
|---|---|---|
| Plant | Medium | strong |
| Plant | upright | upright to semi-upright |
| One-year-old shoot | green | green |
| One-year-old shoot | medium | medium |
| Leaf | Long- very long | long to very long |

TABLE 1-continued

| | | |
|---|---|---|
| Leaf | broad | broad |
| Leaf | elliptic | elliptic |
| Leaf | green | green |
| Leaf | medium | medium |
| Leaf | entire | entire |
| Flower bud | weak | weak |
| Flower | urceolate | urceolate |
| Flower | medium | medium to large |
| Flower | absent or very weak | absent or very weak |
| Flower | present | present |
| Fruit cluster | medium | Medium to dense |
| Unripe fruit | light | light |
| Fruit | Large-very large | very large |
| Fruit | oblate | round |
| Fruit | erect | erect |
| Fruit | large to very large | large |
| Fruit | Deep to very deep | deep |
| Fruit | medium | medium |
| Fruit | dark blue | dark blue |
| Fruit | medium | very firm |
| Fruit | Medium to high | high |
| Fruit | Medium to high | low |
| Time of | medium | Early to medium |
| Time of | late | Early to medium |
| Time of | late | Early to medium |

The invention claimed is:

1. A new and distinct variety of blueberry plant named 'Ridley1702', substantially as illustrated and described herein.

* * * * *